United States Patent [19]

Lashen et al.

[11] Patent Number: 5,145,501

[45] Date of Patent: Sep. 8, 1992

[54] BROMATE STABILIZERS FOR 3-ISOTHIAZOLONES

[75] Inventors: Edward S. Lashen, Furlong; Ramesh B. Petigara, Hatfield, both of Pa.

[73] Assignee: Rohm and Haas Company, Philadelphia, Pa.

[21] Appl. No.: 790,943

[22] Filed: Nov. 12, 1991

[51] Int. Cl.$^5$ .................. A01N 43/80; C07D 275/01; C07D 275/03

[52] U.S. Cl. ....................... 71/67; 514/372; 514/373; 548/213; 548/209; 8/490

[58] Field of Search ............ 71/67; 514/372, 373; 548/209, 213

[56] References Cited

U.S. PATENT DOCUMENTS

| | | | |
|---|---|---|---|
| 3,870,795 | 3/1975 | Miller et al. | 548/213 |
| 4,067,878 | 1/1978 | Miller et al. | 548/213 |
| 4,129,448 | 12/1978 | Greenfield et al. | 548/213 |
| 4,165,318 | 8/1979 | Greenfield et al. | 548/213 |
| 4,906,274 | 3/1990 | Mattox | 548/213 |

OTHER PUBLICATIONS

Merck Index, 11th ed.

*Primary Examiner*—Joseph P. Brust
*Assistant Examiner*—M. S. H. Gabilan
*Attorney, Agent, or Firm*—Michael B. Fein

[57] ABSTRACT

A composition comprising
(a) a 3-isothiazolone compound of the formula

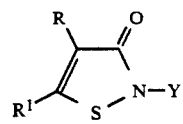

wherein R and $R^1$ are independently selected from hydrogen, halogen or R is a ($C_1$–$C_4$) alkyl group and $R^1$ is a halogen or R and $R^1$ may be joined to form an unsaturated 5- or 6-membered carbocyclic ring; Y is hydrogen, a ($C_1$–$C_{18}$) alkyl group, an unsubstituted or halo-substituted alkenyl or alkynyl of 2 to 8 carbon atoms, a cycloalkyl or substituted cycloalkyl of 3 to 12 carbon atoms, an aralkyl or halo-, ($C_1$–$C_4$) alkyl-, or ($C_1$–$C_4$) alkoxy-substituted aralkyl of up to 10 carbon atoms, or an aryl or halo-, ($C_1$–$C_4$) alkyl-, or ($C_1$–$C_4$) alkoxy-substituted aryl group of up to 10 carbon atoms; and
(b) an amount of a metal bromate salt sufficient to stabilize said composition;
wherein said composition if free of metal nitrate salt is disclosed. Methods of use of the above compositions are also disclosed.

16 Claims, No Drawings

BROMATE STABILIZERS FOR 3-ISOTHIAZOLONES

BACKGROUND OF THE INVENTION

1. Cross Reference to Related Application

The same inventors have filed a U.S. patent application entitled "Bromate as Inhibitor of Nitrosamine Formation for Nitrate Stabilized Isothiazolones and Process" [Ser. No. 07/785,586] on Oct. 30, 1991.

2. Field of the Invention

This invention relates to bromate stabilized compositions of 3-isothiazolones, their preparation, and their use in controlling living organisms.

3. Description of the Prior Art

3-Isothiazolones have generated high commercial interest as microbicides to prevent spoilage caused by microorganisms of a large number of aqueous and non-aqueous products subject to such spoilage. 3-Isothiazolones are highly effective microbicides (as used herein, "microbicides" includes bactericides, fungicides and algaecides and microbicidal activity is intended to include both the elimination of and inhibition or prevention of growth of microbial organisms such as bacteria, fungi and algae); by suitable choice of functional groups, they are useful in a broad range of applications. However, it was early recognized that either in storage prior to addition to the matrix to be stabilized or after addition, their efficacy was decreased because the isothiazolone was not stable under practical conditions of long-term storage. Means have thus been sought from the beginning of research with such compounds to improve their stability.

U.S. Pat. Nos. 3,870,795 and 4,067,878 teach the stabilization of 3-isothiazolones against chemical decomposition by addition of a metal nitrite or metal nitrate, preferably a di- or trivalent metal ion nitrate. The use of said metal nitrates has become conventional in commericial 3-isothiazolone products. These patents also disclose that other common metal salts, including carbonates, sulfates, chlorates, perchlorates and chlorides are ineffective in stabilizing solutions of isothiazolones, such solutions usually being in water or in an hydroxylic solvent. Bromate salts are not taught nor considered in these patents.

Metal nitrates are known to cause problems in some 3-isothiazolone systems, the major problem being conversion of secondary or tertiarty amine impurities to nitrosamines under certain conditions. As a group, nitroso compounds are generally suspected to be possible carcinogens.

Alternatives have been developed to overcome the problems of metal nitrates; however, these alternatives introduce new problems. For example, it is known to use certain organic stabilizers for 3-isothiazolones, generally for use situations where metal salts may create problems, such as corrosion, coagulation of latices, insolubility in non-aqueous media, interaction with the substrate to be stabilized, and the like. Formaldehyde or formaldehyde-releasing chemicals are known as stabilizers, (see U.S. Pat. Nos. 4,165,318 and 4,129,448), as are certain organic chemicals such as orthoesters (U.S. Pat. No. 4,906,274) and epoxides (U.S. Appln. Ser. No. 194,234).

In certain applications, however, it is desirable to avoid addition of organic stabilizers by virtue of their volatility, decomposition in the presence of water or under high heat, higher cost, potential toxicity, and the like. Formaldehyde is a suspected carcinogen, and it is desirable not to use formaldehyde in applications where contact with human skin or lungs may occur.

It is known to use sodium bromate and potassium bromate in the baking industry as bread and flour improving agents (see Merck Index, 11th ed.).

SUMMARY OF THE INVENTION

It has become an object of the invention to provide a stabilization system for 3-isothiazolones which avoids metal nitrates and organic stabilizers. It is also an object to provide a stabilized 3-isothiazolone which uses low levels of stabilizer so as to avoid interference with other components in systems in which isothiazolones are used as microbicides.

These objects, and others which will become apparent from the following disclosure, are achieved by the present invention which comprises in one aspect a composition comprising:

(a) a 3-isothiazolone compound of the formula

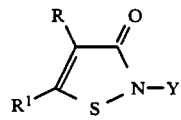

wherein R and $R^1$ are independently selected from hydrogen, halogen or R is a ($C_1$-$C_4$) alkyl group and $R^1$ is a halogen or R and $R^1$ may be joined to form an unsaturated 5- or 6-membered carbocyclic ring; Y is hydrogen, a ($C_1$-$C_{18}$) alkyl group, an unsubstituted or halo-substituted alkenyl or alkynyl of 2 to 8 carbon atoms, a cycloalkyl or substituted cycloalkyl of 3 to 12 carbon atoms, an aralkyl or halo-, ($C_1$-$C_4$) alkyl-, or ($C_1$-$C_4$) alkoxy-substituted aralkyl of up to 10 carbon atoms, or an aryl or halo-, ($C_1$-$C_4$) alkyl-, or ($C_1$-$C_4$) alkoxy-substituted aryl group of up to 10 carbon atoms; and (b) an amount of a metal bromate salt sufficient to stabilize said composition;

wherein said composition is free of metal nitrate salt.

In another aspect, the invention comprises a method for inhibiting the growth of bacteria, fungi, yeast or algae, which comprises incorporating onto or into the locus, in an amount which is effective to adversely affect the growth of bacteria, fungi, yeast or algae, the aforementioned composition.

DETAILED DESCRIPTION AND THE PREFERRED EMBODIMENTS

The isothiazolones which are stabilized are of the formula

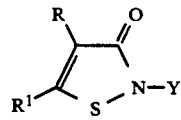

wherein

R and $R^1$ are independently selected from hydrogen, halogen or R is a ($C_1$-$C_4$) alkyl group and $R^1$ is a halogen or R and $R^1$ may be joined to form an unsaturated 5- or 6-membered carbocyclic ring;

Y is hydrogen, a ($C_1$-$C_{18}$) alkyl group, an unsubstituted or halo-substituted alkenyl or alkynyl of 2 to 8 carbon atoms, a cycloalkyl or substituted cycloalkyl of 3 to 12 carbon atoms, an aralkyl or halo-, ($C_1$-$C_4$) alkyl-, or ($C_1$-$C_4$) alkoxy-substituted aralkyl of up to 10 carbon atoms, or an aryl or halo-, ($C_1$-$C_4$) alkyl-, or ($C_1$-$C_4$) alkoxy-substituted aryl group of up to 10 carbon atoms.

Representative Y substituents include methyl, ethyl, propyl, isopropyl, butyl, hexyl, octyl, cyclohexyl, 4-methoxyphenyl, 4-chlorophenyl, 3,4-dichlorophenyl, benzyl, 4-methoxybenzyl, 4-chlorobenzyl, phenethyl, 2-(4-chlorophenyl)ethyl, 4-phenylbutyl, hydroxymethyl, chloromethyl, chloropropyl, hydrogen, and the like.

By a substituted alkyl group is meant an alkyl group having one or more of its hydrogen atoms replaced by another substituted group. Examples of the substituted alkyl groups which characterize 3-isothiazolones of this invention include hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, aryloxyalkyl, alkylthioalkyl, arylthioalkyl, haloalkoxyalkyl, cycloalkylaminoalkyl, such as morpholinoalkyl, piperidinoalkyl, pyrrolidonylalkyl, and the like, carbamoxyalkyl, alkenyl, haloalkenyl, alkynyl, haloalkynyl, isothiazonylalkyl, and the like.

By a substituted aralkyl group is meant an aralkyl group having one or more of the hydrogen atoms on either the aryl ring or the alkyl chain replaced by another substituent group. Examples of the substituent aralkyl groups which characterize 3-isothiazolones of this invention include halogen-, ($C_1$-$C_4$) alkyl, or ($C_1$-$C_4$) alkoxy-substituted aralkyl groups, and the like.

By a substituted aryl group is meant an aryl group, such as benzene, naphthalene, or pyridine, having one or more of the hydrogen atoms on the aryl ring replaced by another substituent group. Examples of such substituent groups include halogen, nitro, ($C_1$-$C_4$) alkyl, ($C_1$-$C_4$) alkyl-acylamino, ($C_1$-$C_4$) carbalkoxy, sulfamyl, and the like.

Y is preferably hydrogen, methyl, ethyl, propyl, isopropyl, butyl, hexyl, octyl, benzyl, 4-methoxybenzyl, 4-chlorobenzyl, phenethyl, 2-(4-chlorophenyl)ethyl, and cyclohexyl.

The preferred 3-isothiazolones of this invention are 5-chloro-2-methyl-3-isothiazolone, and 4,5-dichloro-2-methyl-3-isothiazolone, 5-chloro-2-n-octyl-3-isothiazolone, 4,5-dichloro-2-n-octyl-3-isothiazolone, 5-chloro-2-p-chlorobenzyl-3-isothiazolone, 5-chloro-2-cyclohexyl-3-isothiazolone and 4,5-dichloro-2-cyclohexyl-3-isothiazolone.

Especially preferred is 5-chloro-2-methyl-3-isothiazolone, either as a sole compound or in admixture with 2-methyl-3-isothiazolone. When in admixture, the preferred ratio of monochlorinated to unchlorinated 3-isothiazolone is from about 70:30 to 90:10.

Preferred compositions comprise from about 0.5 to about 25% by weight of one or more of the isothiazolones and a stabilizing amount of a metal bromate salt in the range of from about 0.1 to about 15% by weight.

More preferably, the composition comprises at least one 3-isothiazolone wherein Y is ($C_1$-$C_{18}$) alkyl, ($C_3$-$C_{12}$) cycloalkyl or ($C_7$-$C_{14}$) aralkyl; R is hydrogen, methyl or chloro; and $R_1$ is chloro.

Solvents may be used to dissolve the isothiazolones and may be water or any organic solvent which dissolves the isothiazolones, is compatible with the proposed end use, does not destabilize the 3-isothiazolone, dissolves the metal bromate salt and does not react with the metal bromate salt to eliminate its stabilizing action.

Typical formulation ranges are illustrated in the following Table (all percentages are parts by weight) for both a concentrated solution of the 3-isothiazolone and a dilute solution.

| | Formulations Table | |
|---|---|---|
| 3-isothiazolone | Metal Bromate Salt | Solvent |
| 7-25% (concentrated) | 5-15% | 60-88% |
| 0.5-6.9% (dilute) | 0.1-5% | 88.1-99.4% |

A wide variety of metal bromate salts are known to the art. The preferred metal bromates for this invention are lithium bromate, sodium bromate, potassium bromate, magnesium bromate, calcium bromate, strontium bromate, cobalt bromate and zinc bromate. Especially preferred for use in this invention are lithium bromate, magnesium bromate, potassium bromate and sodium bromate.

Uses of these stabilized microbicides are typically at any locus subject to contamination by bacteria, fungi, yeast or algae. Typically, loci are in aqueous systems such as water cooling, laundry rinse water, oil systems such as cutting oils, oil fields and the like, where microorganisms need to be killed or where their growth needs to be controlled. However, these stabilized microbicides may also be used in all applications for which known microbicidal compositions are useful; preferred utilities of the compositions are to protect wood, paint, adhesive, glue, paper, textile, leather, plastics, cardboard, lubricants, cosmetics, caulking, feed and industrial cooling water from microorganisms.

The following lists typical industries and applications of compositions:

| Industry | Application |
|---|---|
| Adhesives, Sealants | adhesives |
| | caulks |
| | sealants |
| Agriculture/food chain | adjuvant preservation |
| | agricultural active ingredient |
| | agricultural chemical preservative |
| | agricultural formulations preservation |
| | animal feed preservation |
| | dairy chemicals |
| | fertilizer preservation |
| | food preservation |
| | food processing chemicals |
| | grain preservation |
| | post-harvest produce protection |
| | sugar processing |
| | tobacco |
| Construction products | asphalt/concrete |
| | cement modifiers |
| | construction products |
| | roof mastics |
| | synthetic stucco |
| | wall mastics |
| | joint cement |
| Cosmetics and toiletries | cosmetics |
| | raw materials for cosmetics, toiletries |
| | toiletries |
| Disinfectants, antiseptics | antiseptic |
| | disinfectant |
| Emulsions, dispersions | aqueous dispersions |
| | dispersed pigments |
| | latex |
| | photographic emulsions |
| | pigment slurries |
| | polymer latices |
| Formulated consumer and industrial products | air fresheners |
| | fabric softeners |
| | polishes, floor, furniture, shoe |
| | waxes |

| Industry | Application |
|---|---|
| | hand cleaners |
| | sponges and towelettes |
| | spray starch |
| | waxes |
| Industrial processing, misc | electrodeposition paint, baths, rinses. |
| | electrodeposition pre-treatment, post rinses |
| | industrial fluids preservation |
| | pasteurization baths |
| | process aid preservation |
| Industrial water treatment | air washers |
| | cooling towers |
| | cooling water |
| | water cooling |
| | preservation/treatment of wooden cooling tower slats and structural members |
| | can warmers |
| | brewery pasteurization |
| | closed loop water cooling systems |
| Laundry | household laundry products |
| | laundered goods |
| | laundry rinse water |
| | sanitizers-laundry |
| Leather, leather products | leather and hide |
| | leather and hide products |
| Lubricants, hydraulic aids | automotive lubricants and fluids |
| | conveyor lubricants |
| | greases |
| | hydraulic fluids |
| | lubricants |
| Medical devices | diagnostic enzymes |
| | diagnostic kits |
| | medical devices |
| Metalworking & related app's | cutting fluids |
| | metal cleaning |
| | metalworking fluids |
| Odor control (active ingredient) | air conditioning |
| | animal bedding |
| | cat litter |
| | chemical toilet prep'ns |
| | deodorizers |
| | humidifiers |
| | industrial deodorants |
| | sanitary formulations |
| | toilet bowls |
| Paints and coatings | emulsions |
| | paints |
| Paper and wood pulp, their products | absorbent materials of paper and wood pulp |
| | packaging materials of paper and wood pulp |
| | paper |
| | paper products |
| | paper treatment |
| | soap wrap |
| | wood pulp |
| | wood pulp products |
| Paper mill | paper mill slimicides |
| | pulp and paper slurries |
| Petroleum refining, fuels | aviation fuels (jet fuel, aviation gas) |
| | crude oils |
| | burner, diesel and turbine fuel oils |
| | coal slurries |
| | diesel fuel additives |
| | diesel fuels |
| | fuels |
| | gasoline |
| | heating oils |
| | hydrocarbons |
| | kerosene |
| | liquefied petroleum gas |
| | petrochemical feedstocks |
| | petroleum products, storage, transportation and production |
| | recycled petroleum products |
| | residual fuel oils |
| | turbine oils |
| Photographic chemicals | photographic processing - wash water, and process rinses |
| | photoprocessing |
| Printing | photoplate processing chemicals (developers, stabilizers etc) |
| | fountain solutions (printing) |
| | ink components (pigments, resins, solvents, etc) |
| | inks |
| Sanitizers (active) | sanitizers |
| | sanitizers-dairy |
| | sanitizers-dental |
| | sanitizers-fermentation |
| | sanitizers-food preparation |
| | sanitizers-food processing |
| | sanitizers-medical |
| | sanitizers-rendering |
| | sanitizers-veterinary |
| Soaps, detergents, cleaners | cleaners |
| | detergents |
| | household cleaners |
| | industrial cleaners |
| | liquid soaps |
| | oil and grease remover |
| | powdered soaps |
| | raw materials for cleaning products |
| | soaps |
| | surfactants |
| Textiles, textile products | bonded fabrics |
| | burlap |
| | canvas |
| | canvas goods |
| | carpet backing |
| | carpets |
| | clothing |
| | coated fabrics |
| | curtains |
| | draperies |
| | engineering textiles |
| | fibers |
| | geotextiles |
| | goods made of textiles |
| | knitted fabrics |
| | nets |
| | nonwoven fabrics |
| | rope |
| | rugs |
| | textile accessories |
| | textile products |
| | textiles |
| | upholstery |
| | woven fabrics |
| | yarn |
| Textile processing | dye fixatives |
| | dyes |
| | fiber lubricants |
| | hand modifiers |
| | sizes |
| | textile processing fluids |
| Therapeutic (active or preservative) | animal health/veterinary |
| | aquaculture |
| | dental |
| | human health |
| | pharmaceutical/therapeutic |
| Water purification | charcoal beds |
| | deionization resins |
| | filters |
| | membranes |
| | reverse osmosis membranes |
| | ultrafilters |
| | water purification |
| | water purification pipes, tubing |
| Wood applications | lazures (wood stains) |
| | wood |
| | wood products |
| Miscellaneous | alcohols |
| | bedding incorporating water or gels |
| | ceramic |
| | contact lens cases-leaching |
| | electronic circuitry |
| | electronics chemicals |
| | enzymes-food production |
| | enzymes |
| | enzymes-industrial |

-continued

| Industry | Application |
|---|---|
| | gel cushions |
| | marine antifoulants |
| | mildewcides |
| | wood |
| | plastics |
| | laundry |
| | mining |
| | natural rubber latex |
| | oil field injection waters including enhanced recover injection fluids, drilling, fracturing and completion fluids |
| | pipes |
| | plastics |
| | polymer systems |
| | polymers and resins (synthetic and natural) |
| | reagent preservation |
| | rubber |
| | rubber products |
| | skin remover |
| | solid protective/decorative films |
| | stains |
| | swimming pools |
| | waste treatment |
| | water beds |

Because isothiazolones are so active as microbicides and only low levels of metal bromate salts are required to achieve stabilization, the amount of metal bromate salts in systems being treated will be vary small, and therefore it is not likely to interfere with other components in systems requiring protection or with systems to which protected systems will be applied.

It is known in the art that the performance of microbicides may be enhanced by combination with one or more other microbicides. Thus, other known microbicides may be combined advantageously with the composition of this invention.

The following specific examples are presented to illustrate the various aspects of the present invention but are not to be construed as limitations thereof.

EXAMPLE 1

Two 14% AI aqueous solutions of 5-chloro-2-methyl-3-isothiazolone ("CMI") and 2-methyl-3-isothiazolone ("MI") in an approximate ratio of 3:1 were prepared in deionized water, one at pH 2 and one at pH 7. To each sample was added 3% magnesium bromate or sodium bromate. The samples were stored for two weeks at 55° C. in a dri-bath with the initial samples stored in a freezer. The relative concentration of the active ingredient was determined by reverse phase high pressure liquid chromatography, utilizing an ultraviolet detector. The results are presented in Table 1.

TABLE 1

| Stabilizer | pH | Weeks @ 55° C. | % CMI | % CMI Loss |
|---|---|---|---|---|
| None (Control) | — | 0 | 10.7 | — |
| | | 2 | 0 | 100 |
| NaBrO$_3$ | 2 | 0 | 11.3 | — |
| | | 2 | 12.2 | 0 |
| | 7 | 0 | 9.8 | — |
| | | 2 | 9.4 | 5 |
| Mg(BrO$_3$)$_2$ | 2 | 0 | 10.9 | — |
| | | 2 | 11.7 | 0 |
| | 7 | 0 | 9.0 | — |
| | | 2 | 9.6 | 0 |

EXAMPLE 2

Two 14% AI aqueous solutions of 5-chloro-2-methyl-3-isothiazolone ("CMI") were prepared in deionized water. To each sample was added 3% magnesium bromate or sodium bromate (pH 6 to 7). The samples were stored for two weeks at 55° C. in a dri-bath with the initial samples stored in a freezer. The relative concentration of the active ingredient was determined by reverse phase high pressure liquid chromatography, utilizing an ultraviolet detector. The results are presented in Table 2.

TABLE 2

| Stabilizer | Weeks @ 55° C. | % CMI | % CMI Loss |
|---|---|---|---|
| None (Control) | 0 | 13.9 | — |
| | 2 | 0 | 100 |
| NaBrO$_3$ | 0 | 14.0 | — |
| | 2 | 12.6 | 10 |
| Mg(BrO$_3$)$_2$ | 0 | 14.7 | — |
| | 2 | 13.7 | 7 |

EXAMPLE 3

A 3% solution of 5-chloro-2-methyl-3-isothiazolone ("CMI") and 2-methyl-3-isothiazolone in an approximate ratio of 3:1 was prepared by dissolving 4.7 g of the 3-isothiazolone mixture in 130 g deionized water. This 3% 3-isothiazolone solution was combined 1:1 with a 2% stabilizer solution, prepared by dissolving sodium bromate (0.4 g) in deionized water (20 g), yielding a single solution containing 1.5% 3-isothiazolones and 1% sodium bromate as stabilizer, the remaining amount being deionized water. A control consisting of a 1.5% solution of the isothiazolones without any stabilizer was prepared. These solutions were stored at 55° C. The solutions were analyzed for active ingredient by an ultraviolet spectrophotometer. These results are presented in Table 3.

TABLE 3

| | % CMI Loss Weeks Stored at 55° C. | | | | |
|---|---|---|---|---|---|
| Stabilizer | 1 | 2 | 3 | 4 | 8 |
| NaBrO$_3$ | 9 | 16 | 10 | 4 | 24 |
| None (control) | 82 | 100 | — | — | — |

EXAMPLE 4 (COMPARATIVE)

This example illustrates the stabilizing effect of bromate salts. A solution containing 1.5% 5-chloro-2-methyl-3-isothiazolone ("CMI") and 2-methyl-3-isothiazolone in an approximate ratio of 3:1 and 1.0% stabilizer was prepared by combining 0.32 g of the 3-isothiazolone mixture with 0.20 g of the stabilizer in 19.48 g deionized water. A control consisting of a 1.5% solution of the 3-isothiazolones without any stabilizer was prepared. These solutions were stored at 55° C. The relative concentration of the active ingredient was determined by reverse phase high pressure liquid chromatography, utilizing an ultraviolet detector. The results presented in Table 4 show that the bromate salt is an effective stabilizer for 3-isothiazolones but not the chlorate or perchlorate salts.

TABLE 4

| Stabilizer | % CMI Loss Weeks Stored at 55° C. | | | |
|---|---|---|---|---|
| | 1 | 2 | 5 | 6 |
| NaBrO$_3$ | 0 | 0 | 35 | 41 |
| NaClO$_3$ | 100 | 100 | — | — |
| KClO$_4$ | 100 | 100 | — | — |
| None (control) | 100 | — | — | — |

EXAMPLE 5

To a 14% aqueous solution of 5-chloro-2-methyl-3-isothiazolone ("CMI") and 2-methyl-3-isothiazolone in an approximate ratio of 3:1 which was obtained from the magnesium oxide neutralization of the HCl salts of the 3-isothiazolones, 0 to 15% of potassium bromate as a stabilizer was added. The samples were stored at 50° C. for a period of time. The solutions were analyzed for active ingredient by an ultraviolet spectrophotometer. These results are presented in Table 5.

TABLE 5

| Stabilizer | % CMI Loss Storage Time at 50° C. | | |
|---|---|---|---|
| | 5 Days | 2 WKS | 4 WKS |
| None (control) | 29 | 96 | |
| 1% KBrO$_3$ | 2 | 98 | — |
| 5% KBrO$_3$ | 0 | 7 | 19 |
| 10% KBrO$_3$ | 12 | 11 | 29 |
| 15% KBrO$_3$ | 0 | 1 | 16 |

While this invention has been described in sufficient detail for those skilled in the art to be able to make and use it, various alternatives, modifications, and improvements should become apparent from the foregoing disclosure without departing from the spirit and scope of the invention.

What is claimed is:

1. A composition comprising
   (a) a 3-isothiazolone compound of the formula

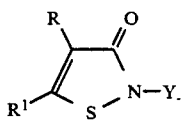

wherein R and R$^1$ are independently selected from hydrogen, halogen or R is a (C$_1$–C$_4$) alkyl group and R$^1$ is a halogen or R and R$^1$ may be joined to form an unsaturated 5- or 6-membered carbocyclic ring; Y is hydrogen, a (C$_1$–C$_{18}$) alkyl group, an unsubstitued or halo-substituted alkenyl or alkynyl of 2 to 8 carbon atoms, a cycloalkyl or substituted cycloalkyl of 3 to 12 carbon atoms, an aralkyl or halo-, (C$_1$–C$_4$) alkyl-, or (C$_1$–C$_4$) alkoxy-substituted aralkyl of up to 10 carbon atoms, or an aryl or halo-, (C$_1$–C$_4$) alkyl-, or (C$_1$–C$_4$) alkoxy-substituted aryl group of up to 10 carbon atoms; and
   (b) an amount of a metal bromate salt sufficient to stabilize said composition;
wherein said composition is free of metal nitrate salt.

2. The composition of claim 1 wherein said metal bromate salt is a bromate salt of a metal cation selected from the group consisting of lithium, sodium, potassium, magnesium, calcium, strontium, cobalt, and zinc.

3. The composition of claim 1 which comprises from about 0.5 to 25 parts by weight of one or more said 3-isothiazolones and from about 0.1 to 15 parts by weight of said metal bromate salt.

4. The composition of claim 1 which comprises from about 1 to 15 parts by weight of said 3-isothiazolone and from about 1 to 10 parts by weight of said metal bromate.

5. The composition of claim 1 which comprises from about 1 to 2 parts by weight of said 3-isothiazolone and from about 1 to 2 parts by weight of said metal bromate.

6. The composition of claim 1 wherein said 3-isothiazolone is selected from the group consisting of 5-chloro-2-methyl-3-isothiazolone, and 4,5-dichloro-2-methyl-3-isothiazolone, 5-chloro-2-n-octyl-3-isothiazolone, 4,5-dichloro-2-n-octyl-3-isothiazolone, 5-chloro-2-p-chlorobenzyl-3-isothiazolone, 5-chloro-2-cyclohexyl-3-isothiazolone and 4,5-dichloro-2-cyclohexyl-3-isothiazolone.

7. The composition of claim 6 wherein the metal bromate salt is selected from the group consisting of lithium bromate, magnesium bromate, potassium bromate and sodium bromate.

8. The composition of claim 1 wherein said 3-isothiazolone is 14 parts by weight of an aqueous solution of 5-chloro-2-methyl-3-isothiazolone and 2-methyl-3-isothiazolone in an approximate ratio of 3 to 1 and 5 parts by weight of potassium bromate.

9. The composition of claim 1 wherein said 3-isothiazolone is 1.5 parts by weight of an aqueous solution of 5-chloro-2-methyl-3-isothiazolone and 2-methyl-3-isothiazolone in an approximate ratio of 3 to 1 and 1 part by weight of potassium bromate.

10. A method for inhibiting the growth of bacteria, fungi, or algae in a locus subject to contamination by bacteria, fungi, or algae, which comprises incorporating into or onto said locus, in an amount which is effective to adversely affect the growth of bacteria, fungi, or algae, a composition according to claim 1.

11. The method of claim 10 wherein said locus is an aqueous medium.

12. The method of claim 10 wherein said locus is a cosmetic formulation.

13. The method of claim 10 wherein said locus is fabric, leather, paper, or wood.

14. The method of claim 10 wherein said locus is a solid protective or decorative film.

15. The method of claim 10 wherein said composition comprises from about 1 to 25 parts by weight of said 3-isothiazolone, wherein said 3-isothiazolone is selected from the group consisting of 5-chloro-2-methyl-3-isothiazolone, and 4,5-dichloro-2-methyl-3-isothiazolone, 5-chloro-2-octyl-3-isothiazolone, 4,5-dichloro-2-octyl-3-isothiazolone, 5-chloro-2-p-chlorobenzyl-3-isothiazolone, 5-chloro-2-cyclohexyl-3-isothiazolone, and 4,5-dichloro-2-cyclohexyl-3-isothiazolone and from about 1 to 10 parts by weight of said metal bromate salt.

16. The method of claim 15 wherein said metal bromate salt is selected from the group consisting of lithium bromate, magnesium bromate, potassium bromate and sodium bromate.

* * * * *